United States Patent [19]

Buell

[11] 4,397,645
[45] Aug. 9, 1983

[54] DISPOSABLE ABSORBENT ARTICLE HAVING AN IMPROVED LIQUID CONTAINMENT CONSTRUCTION

[75] Inventor: Kenneth B. Buell, Cincinnati, Ohio

[73] Assignee: The Procter & Gamble Company, Cincinnati, Ohio

[21] Appl. No.: 237,789

[22] Filed: Feb. 24, 1981

[51] Int. Cl.³ .............................................. A41B 13/02
[52] U.S. Cl. .................................................. 604/380
[58] Field of Search ........... 128/284, 286, 287, 290 R; 604/378, 379, 380, 383, 385

[56] References Cited

U.S. PATENT DOCUMENTS

| | | | |
|---|---|---|---|
| 1,314,799 | 9/1919 | Guinzburg | 128/288 |
| 2,004,088 | 6/1935 | Alsop | 128/284 |
| 2,530,647 | 11/1950 | Buchler | 128/287 |
| 2,701,567 | 2/1955 | Smith | 128/284 |
| 3,520,303 | 7/1970 | Endres | 128/287 |
| 3,572,342 | 3/1971 | Lindquist et al. | 128/287 |
| 3,636,952 | 1/1972 | George | 128/287 |
| 3,693,622 | 9/1972 | Jones, Sr. | 128/290 |
| 3,799,167 | 3/1974 | Miller et al. | 128/287 |
| 3,828,784 | 8/1974 | Zoephel | 128/287 |
| 3,860,003 | 1/1975 | Buell | 128/287 |
| 4,015,604 | 4/1977 | Csillag | 128/287 |
| 4,050,462 | 9/1977 | Woon et al. | 128/287 |
| 4,226,238 | 10/1980 | Bianco | 128/287 |
| 4,239,578 | 12/1980 | Gore | 156/361 |
| 4,259,958 | 4/1981 | Goodbar | 128/287 |
| 4,300,562 | 11/1981 | Pieniak | 128/287 |

FOREIGN PATENT DOCUMENTS 2016262 9/1979 United Kingdom .
2023431 1/1980 United Kingdom .

*Primary Examiner*—C. Fred Rosenbaum
*Attorney, Agent, or Firm*—John M. Pollaro; Fredrick H. Braun; Richard C. Witte

[57] ABSTRACT

An article of manufacture is disclosed for absorbing liquids, particularly body fluids such as urine. An absorbent core is encased in an outer covering layer. Leakage resistant members are affixed at each segment of the diaper from which leakage is to be reduced. The leakage resistant member has a facing sheet having compacted portions affixed to a backing sheet. The leakage resistant members may be elasticized by providing a separate elastic element or by using an elastic material for the backing sheet.

5 Claims, 13 Drawing Figures

U.S. Patent  Aug. 9, 1983  Sheet 1 of 4  4,397,645
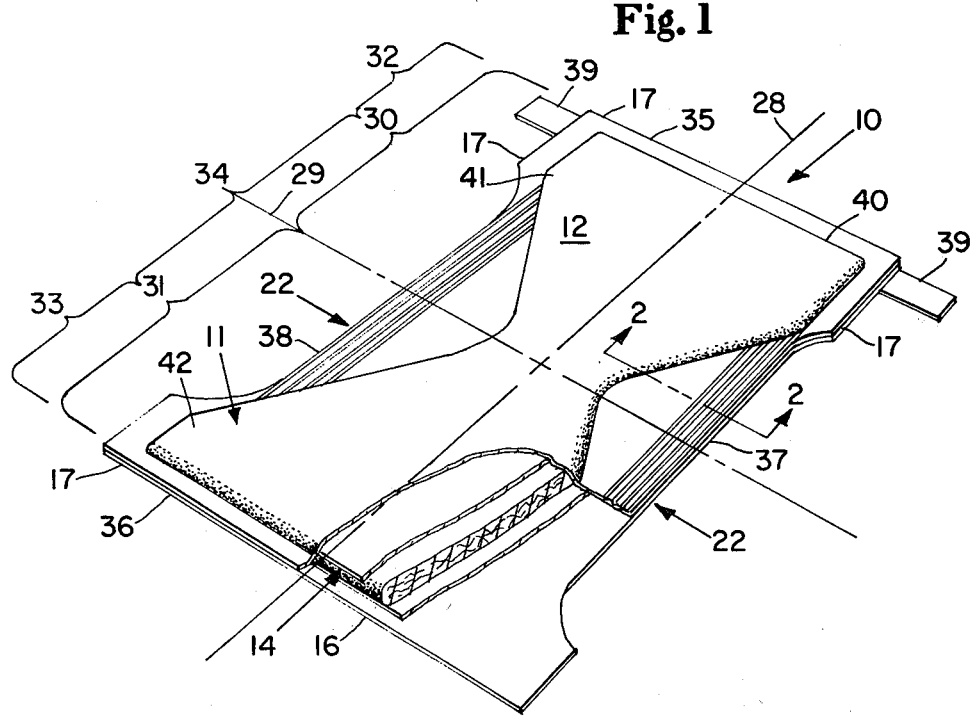
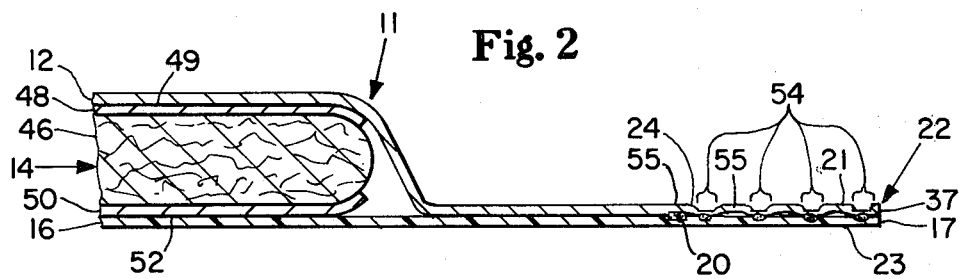

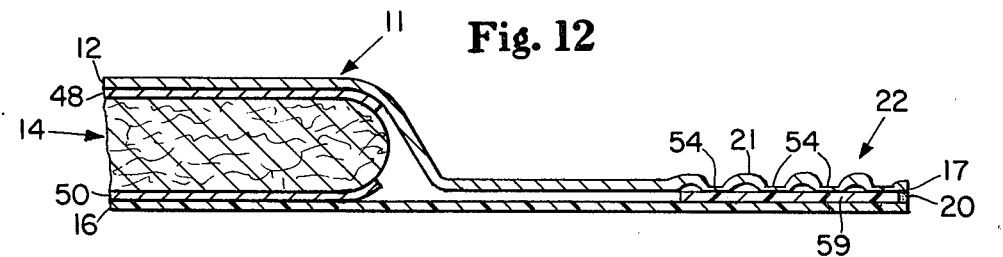
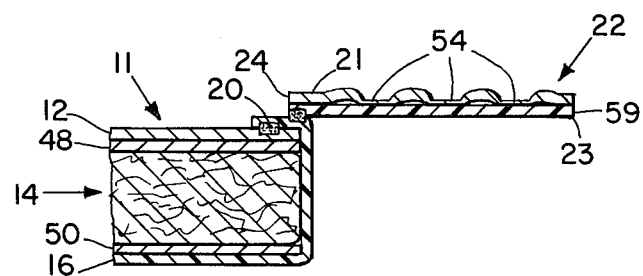

DISPOSABLE ABSORBENT ARTICLE HAVING AN IMPROVED LIQUID CONTAINMENT CONSTRUCTION

BACKGROUND OF THE INVENTION

This invention relates to disposable absorbent articles in general and more particularly relates to disposable diapers and the like. Still more particularly, this invention relates to disposable diapers having a leakage resistant member positioned so that liquid will contain the leakage resistant member before leakage occurs.

Disposable absorbent articles are well known in the prior art and have many uses. For example, disposable diapers are intended to absorb and contain urine; bandages are intended to absorb and contain blood and other body exudates; while catamenial pads are intended to absorb and retain menstrual fluids. In each instance, the disposable absorbent article absorbs and retains a liquid, thereby preventing that liquid from soiling, wetting, or otherwise contaminating the vicinity surrounding the point of liquid discharge.

Disposable absorbent articles should perform without leaking and several concepts have been proposed to improve the containment characteristics of such articles. For example, it has been recognized that the liquid containment characteristics of a disposable absorbent article can be improved by rendering the perimeter of the article liquid impermeable. Thus, as taught in U.S. Pat. No. 3,520,303 entitled DISPOSABLE DIAPER which issued to D. D. Endres on July 14, 1970, a leak preventing barrier may be provided at the ends of a disposable diaper to prevent liquid leakage from the waist. The barrier is a strip of thin film which is affixed between the topsheet and the backsheet along a single line at the perimeter of the diaper. Further, U.S. Pat. No. 3,693,622 entitled WASTE FLUID FLOW CONTROL ELEMENT which issued to J. L. Jones, Sr. on Sept. 26, 1972 teaches a waste fluid absorption device in which the periphery of the absorbent core is treated with a liquid repellent composition which renders the periphery liquid impermeable. Additionally, U.S. Pat. No. 3,799,167 entitled DISPOSABLE ABSORBENT PAD which issued to A. H. Miller et al. on Mar. 26, 1974 is similar in concept to the aforementioned Jones patent in that the periphery of the absorbent article is rendered liquid impermeable by treatment with a waterproofing composition. Miller et al., however, apply the waterproofing composition to the periphery of the topsheet rather than to the periphery of the absorbent core.

U.S. Pat. No. 3,860,003 entitled CONTRACTIBLE SIDE PORTIONS FOR A DISPOSABLE DIAPER which issued to K. B. Buell on Jan. 14, 1975 and U.S. Pat. No. 4,050,462 entitled DISPOSABLE DIAPER WITH ELASTICALLY CONSTRICTED CROTCH SECTION which issued to L. S. Woon et al. on Sept. 27, 1977 each teach a concept for reducing liquid leakage which involves providing an elastic member in a disposable diaper. The elastic member is positioned so that when the diaper is worn the diaper is drawn snugly about the leg of the diaper wearer. The elastic therefore causes the diaper to form a seal about the leg of the diaper wearer thereby preventing a liquid from leaking out of the diaper.

The disposable absorbent articles of the prior art lack the aspects of the present invention whereby a reduction in liquid leakage is obtained by providing a leakage resistant member having compacted portions which are disposed below the wearer-contacting surface of the diaper.

It is therefore an object of the present invention to provide an absorbent article having improved liquid containment characteristics.

A further object of the present invention is to provide an absorbent article having a leakage reduction member.

An additional object of the present invention is to provide an absorbent article having a leakage reduction member in which compacted portions of the facing sheet are disposed below the wearer-contacting surface of the diaper.

An additional object of the present invention is to provide an absorbent article having a leakage reduction member which is elasticized.

These and other objects of the invention will be more readily apparent when considered in reference to the following description and when taken in connection with the accompanying drawings.

SUMMARY OF THE INVENTION

According to the present invention, a disposable absorbent article such as a diaper is manufactured such that the absorbent core is encased in an outer covering layer having a liquid permeable topsheet portion and a liquid impermeable backsheet portion. The disposable absorbent article is provided with at least one leakage resistant member which is positioned such that when the diaper is worn the liquid will contact a leakage resistant member before leakage occurs. However, a multiplicity of leakage reduction members may be affixed at various portions of the diaper.

The leakage resistant member comprises a fibrous facing sheet and a liquid impermeable backing sheet. The facing sheet has compacted portions which are affixed to the backing sheet and which are disposed below the wearer-contacting surface of the diaper. The leakage reduction member may be elasticized by providing an elastic member. The elastic member causes the facing sheet to buckle thereby forming pillows. The pillows enhance the elevational difference between the wearer-contacting surface and the compacted portion.

BRIEF DESCRIPTION OF THE DRAWINGS

FIG. 1 is a partially cutaway perspective view of a disposable diaper incorporating a preferred embodiment of the present invention.

FIG. 2 is a cross-sectional view of the diaper of FIG. 1 taken along line 2—2.

FIG. 12 is a cross-sectional view of an alternative diaper construction taken along a line corresponding to line 5—5 of FIG. 4.

FIG. 13 is a cross-sectional view of an alternative diaper construction taken along a line corresponding to line 5—5 of FIG. 4.

DESCRIPTION OF A PREFERRED EMBODIMENT

Figure 3:
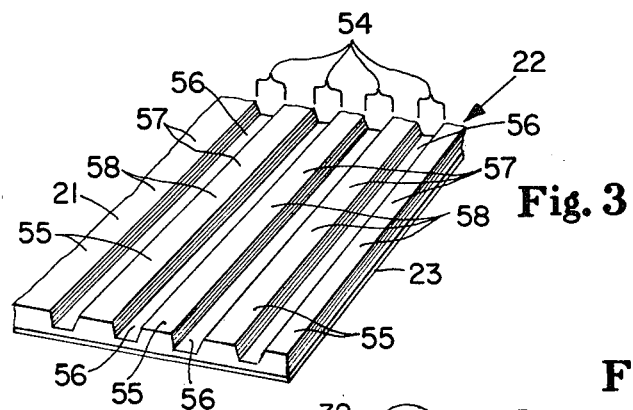
FIG. 3 is a perspective view of a portion of the leakage resistant member shown in FIG. 2.

Referring now to the figures, there is shown a preferred embodiment of the present invention as it would be used in a disposable absorbent article and, in particular, as it would be used in a disposable diaper. As used herein, the term "disposable absorbent article" refers to articles which absorb and contain liquid, and more specifically refers to articles which are placed against or in proximity to the human body to absorb and contain the various liquids discharged therefrom (e.g., blood, menses, urine, etc.), and further which articles are intended to be discarded after a single use (i.e., they are not intended to be laundered or otherwise restored and reused). A "diaper" is a garment generally worn by infants and incontinent persons, which is drawn up between the legs and fastened about the waist of the wearer. It should be understood, however, that the present invention is also applicable for use in other disposable absorbent articles such as bandages, bed pads, catamenial pads, and the like.

FIG. 1 is a partially cut-away view of the disposable diaper 10 of the present invention prior to its being folded and placed on the diaper wearer. As seen in FIG. 1, a preferred disposable diaper 10 basically comprises an outer covering layer 11 and an absorbent core 14. While the outer covering layer 11 and the absorbent core 14 may be generally assembled in a variety of well known configurations such as are described in U.S. Pat. No. 3,860,003 entitled CONTRACTABLE SIDE PORTIONS FOR DISPOSABLE DIAPER which issued to K. B. Buell on Jan. 14, 1975, and U.S. Pat. No. RE. 26,151 entitled DISPOSABLE DIAPER which issued to R. C. Duncan et al. on Jan. 31, 1967, which patents are incorporated herein by reference, a preferred construction of the diaper 10 will now be described.

As can be seen in FIGS. 1 and 2 a preferred outer covering layer 11 encases and contains the absorbent core 14 and preferably has a topsheet portion 12 and backsheet portion 16 which are joined together in any suitable manner. As used herein, the term "joined" encompasses configurations whereby the topsheet portion 12 is directly joined to the backsheet portion 16 by affixing the topsheet portion 12 directly to the backsheet portion 16 and configurations whereby the topsheet portion 12 is indirectly joined to the backsheet portion 16 by affixing the topsheet portion 12 to an intermediate member which in turn is affixed to the backsheet portion 16.

The topsheet portion 12 and the backsheet portion 16 preferably have length and width dimensions larger than those of the absorbent core 14. Thus, the topsheet portion 12 may be joined to the backsheet portion 16 by directly affixing the topsheet portion 12 to the backsheet portion 16. Preferably, a peripheral seam 20 (FIG. 2) placed around the marginal portion of the diaper 10 is used to join the topsheet portion 12 to the backsheet portion 16. The peripheral seam 20 is preferably a continuous band of hot melt adhesive such as that manufactured by the Eastman Chemical Products Company of Kingsport, Tenn. and marketed under the tradename Eastobond A-3. Alternatively, the topsheet portion 12 may be affixed to the backsheet portion 16 using any suitable means such as ultrasonic sealing or heat sealing and in any suitable configuration such as intermittent dots or dashes.

The peripheral seam 20 may be positioned at any convenient location on the diaper 10 considering the specific diaper configuration and the particular method used to manufacture the diaper 10. As shown in FIG. 2 the peripheral seam 20 is preferably positioned outward from the absorbent core 14. Further, the peripheral seam preferably encircles the absorbent core 14 thereby encasing the absorbent core 14 between the topsheet portion 12 and the backsheet portion 16.

As can be seen in FIG. 1, the disposable diaper 10 has a longitudinal centerline 28, a lateral centerline 29, a back portion 30, a front portion 31, a back waist portion 32, a front waist portions 33, and a crotch area 34. Further, the disposable diaper 10 has a peripheral edge 17 defining the outer periphery or in other words the outer extent of the diaper 10. The peripheral edge comprises a back edge 35, a front edge 36, and first and second longitudinal side edges 37 and 38, respectively.

The back portion 30, in general, is that part of the diaper from the lateral centerline 29 to the back edge 35 of the diaper 10 and which when the diaper is worn contacts the back of the infant. The front portion 31, in general, is that portion of the diaper 10 from the lateral centerline 29 to the front edge 36 of the diaper 10 and which when the diaper 10 is worn contacts the front of the infant. The back waist portion 32 is that marginal portion of the diaper 10 adjacent to back edge 35. The front waist portion 33 is that marginal portion of the diaper 10 adjacent to the front edge 36. The back and front waist portions 32 and 33, respectively, cooperate with each other when the diaper 10 is fitted on and attached to an infant to encircle the infant's waist and hold the diaper 10 on the infant. The back waist portion 32 and the front waist portion 33 each have a width which extends from the back edge 35 and the front edge 36, respectively, toward the lateral center line 29 a distance of approximately 1 inch to 2½ inches (2.5 cm. to 6.4 cm.) and each has a length which extends transversely across the diaper 10 at the back edge 35 and at the front edge 36, respectively. The depth of the back and front waist portions, 32 and 33 respectively, is established primarily by and includes the diaper fastening means for affixing the diaper around the waist of the infant. An acceptable fastening means is an adhesive fastening tape 39 as is well known in the disposable diaper art.

The crotch area 34 of the diaper 10 is that area of the diaper which is generally located directly between the legs and around the lower portion of an infant when the diaper 10 is worn and is approximately centered on the lateral centerline 29.

The absorbent core 14 may be manufactured in a wide variety of sizes and from a wide variety of absorbent materials which are commonly used in disposable absorbent articles and which are capable of absorbing and retaining liquids. While comminuted wood pulp, generally referred to as airfelt, is preferred for the manufacture of the absorbent core 14, other liquid absorbent materials such as foams, a multiplicity of plies of creped cellulose wadding, or any equivalent material may also be used. The total absorbent capacity of the absorbent core 14 should, however, be compatible with the design liquid loadings in the intended use of the absorbent article.

The preferred embodiment illustrated in FIG. 1 has an hourglass shaped absorbent core 14 wherein the absorbent core 14 in the back and front waist portions 32 and 33 respectively, is wider than the absorbent core 14 in the crotch area 34, thereby forming ears 40, 41, 42, (FIG. 1) and a fourth ear which is not shown, at the corners of the absorbent core 14. The preferred embodiment illustrated in FIG. 1 is intended to be worn by infants ranging in weight from 12 pounds to about 26 pounds (5 kgs. to about 12 kgs.). The absorbent core 14 is, therefore, a pad of airfelt approximately 16 inches (40.6 cm.) long when measured along the longitudinal centerline 28, having a width of approximately 12 inches (31.9 cm.) across back and front waist portions 32 and 33, respectively, and having a width of approximately 4 inches (10.2 cm.) across the crotch area 34 of the diaper 10. The absorptive capacity of the airfelt used for the absorbent core 14 is sufficient to absorb and retain approximately from 8 to 16 grams of water per gram of absorbent. Accordingly, the airfelt used in the preferred embodiment shown in FIG. 1 weighs approximately from 30 to 56 grams. It should be understood, however, that the size, shape, and total absorbent capacity of the absorbent core 14 may be varied to accommodate diaper wearers ranging from infants to adults. Therefore, other dimensions and even other shapes (e.g., rectangular) may also be used for the absorbent core 14.

As best seen in FIG. 2, a preferred absorbent core 14 comprises an absorbent layer 46 and a first tissue layer 48 which forms a first opposed surface 49 of the absorbent core 14 and a second tissue layer 50 which forms a second opposed surface 52 of the absorbent core 14.

The absorbent layer 46 is preferably comminuted wood pulp as hereinbefore described. The first and second tissue layers 48 and 50 improve the tensile strength of the absorbent layer 46 and reduce the tendency of the absorbent layer 46 to lump or ball when wetted. While a number of materials and manufacturing techniques may be used to manufacture the tissue layers 48 and 50, satisfactory results have been obtained with sheets of wet strength tissue paper having a basis weight of about 12 pounds per 3,000 square feet (19 gms. per square meter) and having an air permeability of about 100 cubic feet per minute per square ft. (30.5 cubic meters per minute per square meter) over a ½ inch (12.8 mm.) water pressure drop. While the tissue layers 48 and 50 are preferably coterminous with the absorbent layer 46, they may have different dimensions, a different configuration, or may be omitted entirely.

The second tissue layer 50 of the absorbent core 14 is superposed on backsheet 16 and is preferably attached thereto by attachment means such as those well known in the art. Accordingly, the absorbent core 14 may be secured to the backsheet 16 by a uniform continuous layer of adhesive, a patterned layer of adhesive or a number of separated lines or spots of adhesive. An adhesive which has been found to be satisfactory is manufactured by Eastman Chemical Products Company of Kingsport, Tenn. and marketed under the tradename Eastobond A-3.

The backsheet portion 16 is impermeable to liquids and prevents liquids absorbed by the absorbent core 14 from wetting the undergarments, clothing, bedding, and other objects which contact the wearer of the disposable diaper 10. Preferably the backsheet portion 16 is a polyethylene film of from about 0.0005 to about 0.002 inches (about 0.0012 to about 0.051 mm.) thick, although other flexible, liquid impermeable materials may also be used. As used herein, the term "flexible" refers to materials which are compliant and which readily conform to the shape and contours of the human body. A suitable polyethylene film is manufactured by Monsanto Chemical Company and marketed in the trade as film No. 8020.

In a preferred embodiment, the backsheet portion 16 has a modified hourglass configuration extending beyond the edge of the absorbent core 14 a distance of approximately ½ inch to 1 inch (1.3 cm. to 2.5 cm.). Along the first and second longitudinal sides 37 and 38, the backsheet portion 16 extends beyond and is generally parallel to the longitudinal sides of the absorbent core 14. As the absorbent core 14 gets narrower towards the crotch area 34, the edge of the backsheet portion 16 is substantially linear and parallel to the longitudinal centerline 28 so that the backsheet portion 16 is wider than the absorbent core 14. The linear portion of the first and second longitudinal side edges 37 and 38, respectively, is generally between 5 inches and 12 inches (between 12 and 30 cm.) long and for the diaper 10 of the preferred embodiment illustrated in FIG. 1, is about 9 inches (23 cm.) long. The backsheet portion 16 is preferably embossed and/or matte finished to provide a more cloth-like appearance. Further, the backsheet portion 16 may be perforated or otherwise modified to permit vapors to escape from the absorbent core 14, provided liquid is not allowed to pass from the absorbent core 14 through the backsheet portion 16.

The topsheet portion 12 is compliant, soft feeling, and non-irritating to the wearer's skin. Further, the topsheet portion 12 is liquid permeable, permitting liquids to readily penetrate through its thickness. A suitable topsheet portion 12 may be manufactured from a wide range of materials such as plastic films, natural fibers (e.g., wood or cotton fibers) synthetic fibers (e.g., polyester or polypropylene) or a combination of natural and synthetic fibers and prevents the wearer of the diaper 10 from contacting the absorbent core 14.

A particularly preferred topsheet portion 12 is fibrous comprising by weight about 65 percent staple length polyester fibers having a denier of about 1.5, such as Kodel Type 411 polyester fiber marketed by Tennessee Eastman Corporation of Kingsport, Tenn., about 15 percent staple length crimped rayon fibers having a denier of approximately 1.5; and about 20 percent acrylic copolymer binder such as Celanese CPE 8335 marketed by Celanese Corporation of Charlotte, N.C. As used herein, the term "staple length fibers" refers to those fibers having a length of at least about 0.625 inches (15.9 mm.).

Clearly, there are a number of manufacturing techniques which may be utilized to manufacture the preferred topsheet portion 12. For example, the topsheet portion 12 may be woven, nonwoven, spunbonded, carded, or the like. A preferred topsheet portion 12 is carded, saturated with a binder solution, dried and cured by means well known to those skilled in the art. Preferably, the topsheet portion 12 has a basis weight range of from about 18 to about 30 grams per square yard, a minimum wet tensile strength of at least 400 grams per cm. in the machine direction and at least about 55 grams per cm. in the cross-machine direction.

Liquid discharged onto the diaper 10 which is being worn will be distributed throughout the diaper 10. As a result of the liquid distribution some of the liquid will reach segments of the diaper 10 from which leakage can occur. The location of these segments and the specific means by which leakage occurs will depend on the particular construction used for the diaper 10. In general, however, the liquid leakage is likely to occur at those segments of the diaper 10 which are fitted about the waist and legs of the diaper wearer.

More specifically, liquid leakage may occur at one segment of the diaper 10 such as at the front edge 36 or at the back edge 35. Alternatively, liquid leakage may occur at a multiplicity of segments of the diaper 10 such as at both the front and back edges 36 and 35 or at both the first and second lonitudinal side edges 37 and 38 or at the front edge 36, the back edge 35, the first longitudinal side edge 37 and second longitudinal side edge 38.

A leakage resistant member 22 is affixed at each segment from which liquid leakage is to be reduced. For example, a leakage resistant member 22 may be affixed at the front edge 36 or at the back edge 35. Alternatively, a multiplicity of leakage resistant members 22 may be affixed to the diaper 10 at a multiplicity of segments at which liquid leakage may occur. For example, leakage resistant members 22 may be affixed at both the front and back edges 36 and 35 or at both the front and back edges 36 and 35 and at the first and second lonitudinal side edges 37 and 38. The leakage resistant members 22 reduce and preferably prevent liquid leakage in a manner hereinafter described.

FIGS. 1 and 2 illustrate a preferred embodiment of the present invention in which liquid leakage is to be reduced at the legs of the wearer of the diaper 10. Accordingly, a leakage resistant member 22 is affixed at each of the segments of the diaper 10 which surround the wearer's legs when the diaper 10 is worn. Thus, the diaper 10 has a leakage resistant member 22 affixed at the first longitudinal side 37 and another liquid resistant member 22 affixed at the second longitudinal side 38. As hereinbefore stated, however, additional or other leakage resistant members 22 may be affixed at additional or other segments of the diaper 10. For example, it may be advantageous to reduce liquid leakage at either the back edge 35 or at the front edge 36 of the diaper 10 in conjunction with reducing liquid leakage at the first and second longitudinal sides 37 and 38. Since the leakage resistant member 22 is generally the same irrespective of which segment of the diaper 10 it is affixed at, the construction of the leakage resistant members 22 intended to reduce liquid leakage at the legs of the wearer will be described.

Referring now to FIGS. 2 and 3, it can be seen that the leakage resistant members 22 have a fibrous liquid permeable facing sheet 21, a liquid impermeable backing sheet 23 and a first end portion 24 (FIG. 2) defining the boundary of the leakage resistant member 22 along one end. The facing sheet 21 may be manufactured from a wide variety of fibrous materials which are compliant, soft feeling, and non-irritating to the wearer's skin. The facing sheet 21 may be woven or nonwoven from natural fibers (e.g., wood or cotton fibers) or from synthetic fibers (e.g., polyester or polypropylene fibers) or from a combination thereof. Alternatively, the facing sheet 21 may be a fiber-like foam such as the reticulated foams which are well known in the art. In general, fibrous webs which are suitable for use as the topsheet portion 12 are also suitable for use as the facing sheet 21.

The backing sheet 23 underlays the facing sheet 21, is impermeable to liquids and is preferably a polyethylene film of from about 0.0005 to about 0.002 inches thick (about 0.0012 to about 0.051 mm.), although other flexible, liquid impermeable materials may also be used. In general, materials which are suitable for use as the backsheet portion 16 are also suitable for use as the backing sheet 23.

As used herein, the term "affixed at" means that the leakage resistant member 22 is connected to the diaper 10 at or near a segment of the diaper 10 from which liquid leakage may occur such that liquid will preferably contact the leakage resistant member 22 before leakage occurs (i.e., before liquid contacts the wearer's undergarment, etc.) at those segments. The term "connected" includes any means of joining the leakage resistant member 22 to the diaper 10 and encompasses means whereby the leakage resistant member 22 is made integral with the diaper 10 (i.e., the leakage resistant member 22 is a separate element affixed to the diaper 10) and means whereby the leakage resistant member 22 is unitary with the diaper 10 (i.e., the leakage resistant member 22 has at least one continuous and undivided element in common with the outer covering layer 11).

In the preferred embodiment of the leakage resistant member 22 illustrated in FIGS. 2 and 3, the leakage resistant member 22 is positioned outward from the absorbent core 14 and is made unitary with the diaper 10 by extending the topsheet portion 12 and the backsheet portion 16 outward from the absorbent core 14 to form the facing sheet 21 and the backing sheet 23, respectively. Alternatively, the leakage resistant member 22 may be made integral with the diaper 10 by affixing the first end portion 24 to the outer covering layer 11 using any suitable means such as by gluing, heat sealing or ultrasonic bonding techniques.

Referring to FIGS. 2 and 3, it can be seen that the facing sheet 21 is oriented so as to be placed against the skin of the diaper wearer and has a compacted portion 54, which alters the flow pattern of liquid. The desired affect of the compacted portion 54 may be achieved in many ways such as by filling or partially filling the interstitial voids of the facing sheet 21 in the compacted portion 54 with an adhesive or other liquid impermeable material. In this manner, the compacted portion 54 is not compacted or compressed but is nonetheless made to act as a non-wicking barrier to the movement of liquid. In a particularly preferred embodiment, however, the compacted portion 54 is compressed or densified relative to the other portions of the facing sheet 21, which other portions, for convenience, are designated uncompacted portions 55. In other words, both the spacing between fibers and the interstitial void volume are reduced in the compacted portion 54 to an extent sufficient to cause the compacted portion 54 to exhibit a greater capillary attraction for liquid than the uncompacted portion 55. Thus, liquid contacting the compacted portion 54 will wick into and through the compacted portion 54. Having once entered the compacted portion 54, the liquid will tend to be held in the compacted portion 54 because the compacted portion 54 has a higher capillary attraction for the liquid than does the adjacent uncompacted portion 55. The compacted portion 54, therefore, alters the liquid flow pattern and by configuring the compacted portion 54 as hereinafter described, the liquid is redirected away from those parts of the diaper from which leakage may occur.

The ratio of the caliper of the uncompacted portion 55 of the facing sheet 21 to the caliper of the compacted portion 54 is at least about 1.5:1 and preferably at least about 2.0:1. Most preferably, the ratio of the caliper of the uncompacted portion 55 to the caliper of the compacted portion 54 is at least about 4:1. It should be understood the term "caliper" refers to thickness of the facing sheet 21 only and does not in any way refer to the relative elevations of the compacted and uncompacted portions 54 and 55.

Many procedures are suitable for determining the ratio of the caliper of the uncompacted portion 55 to the caliper of the compacted portion 54. For example, a simple optical procedure may be used whereby a strip of the topsheet is cut perpendicular to the compacted portion 54. By viewing the edge of the strip through a microscope having a calibrated eyepiece, the calipers of the uncompacted portion 55 and of the compacted portion 54 can be determined. From the individual calipers, the ratio of the calipers is easily calculated.

The compacted portion 54 of the facing sheet 21 is affixed to the backing sheet 23 using any suitable means which will provide a liquid retarding bond between the facing sheet 21 and the backing sheet 23. Thus, liquid migration along the interfacial junction between the facing sheet 21 and the backing sheet 23 is retarded and is preferably prevented. In a preferred embodiment, heat sealing along the compacted portion 54 as is well known in the art was used and found to be satisfactory. The use of heat sealing techniques to affix the compacted portion 54 to the backing sheet 23 has the additional advantage of compressing the compacted portion 54 at the same time it is affixed to the backing sheet 23.

A compacted portion 54 corresponds to each liquid resistant member 22 and is intended to retard and preferably to prevent liquid from reaching a point from which leakage may occur. Accordingly, the compacted portion 54 is configured so as to render the path followed by the liquid tortuous and preferably impassible. Thus, each compacted portion 54 preferably, comprises a multiplicity of continuous bands 56 (FIG. 3) defining reservoirs 57 therebetween. The reservoirs 57 are preferably neither compacted nor affixed to the backing sheet 23.

In the preferred embodiment illustrated in FIGS. 1, 2 and 3, a compacted portion 54 comprising a multiplicity of continuous bands 56 is provided at each leakage resistant member 22. The bands 56 are straight lines which are generally parallel to the first and second longitudinal side edges 37 and 38, respectively.

The combination of bands 56 and reservoirs 57 promote a redirection and absorption of liquids so that the liquids will not reach a point from which they can wet the vicinity surrounding the diaper 10. The bands have a width of at least about 0.01 inches (0.25 mm) and preferably at least about 0.03 inches (0.79 mm) while the reservoirs 57 have a width of at least about 0.03 inches (0.79 mm) and preferably at least about 0.09 inches (2.38 mm). The narrower the width of bands 56 and reservoirs 57 the more readily liquid will bridge them without being redirected or absorbed.

The compacted portion 54 may take on a variety of configurations such as an array of discrete areas. For example, the array of discrete areas may comprise a multiplicity of spaced circles, ovals, or dashes arranged in either a random or regular pattern which provides a tortuous or impassible path from the point of liquid discharge to a point from which liquid can wet the vicinity surrounding the diaper 10. Alternatively, the compacted portion 54 may comprise a multiplicity of bands having gaps or spaces arranged so that the gaps or spaces in adjoining bands do not coincide thereby providing a tortuous or impassible path from the point of liquid discharge to a point from which the liquid can wet the vicinity surrounding the diaper 10. Further, the compacted portion 54 may comprise a multiplicity of bands 56 which may be rectilinear, curvilinear, straight, or curved and which may have parallel sides forming a band 56 of uniform width or may have non-parallel sides forming a band 56 of varying width. As hereinbefore stated, a compacted portion 54 corresponds to each liquid leakage resistant member 22. The diaper 10 may, therefore, have a multiplicity of compacted portions 54 each of which comprises a multiplicity of bands 56.

In the preferred embodiment shown in FIG. 3 the uncompacted portions 55 have a wearer-contacting surface 58 which is placed in contact with the diaper wearer when the diaper is worn. The compacted portion 54 is disposed below the wearer contacting surface 58 and, therefore, does not contact the skin of the diaper wearer. Preferably, the compacted portion 54 is disposed at least 0.005 inches (0.127 mm.) below the wearer-contacting surface when the wearer-contacting surface 58 is placed against the wearer's skin.

Figure 4:
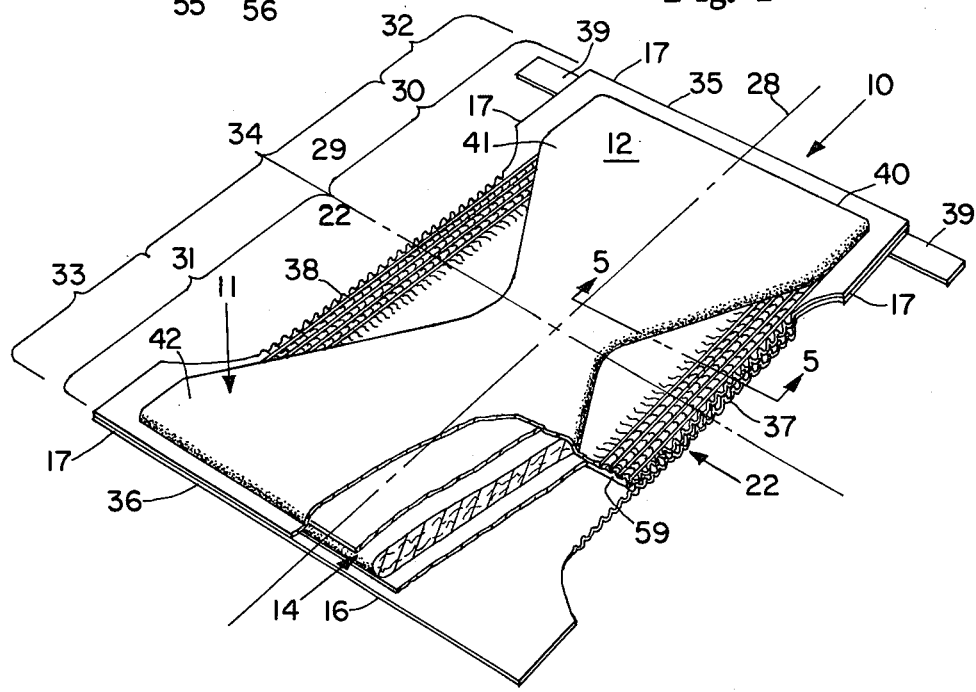
FIG. 4 is a partially cutaway perspective view of a disposable diaper incorporating an alternatively preferred embodiment of the present invention.
Figure 5:
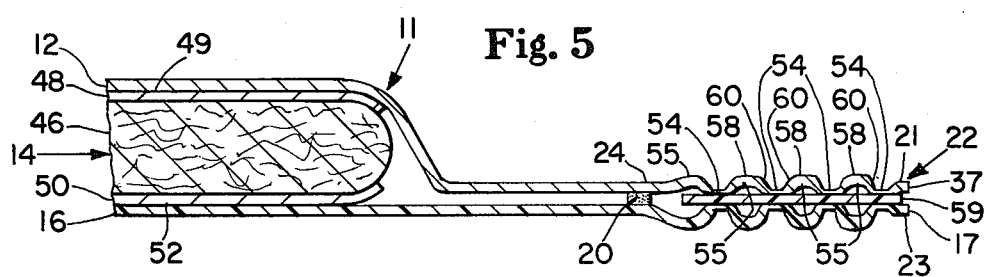
FIG. 5 is a cross-sectional view of the diaper of FIG. 4 taken along line 5—5.
Figure 6:
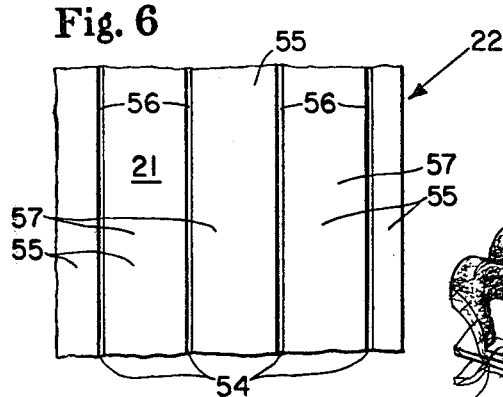
FIG. 6 is a plan view of a segment of the leakage resistant member in an ungathered configuration showing a preferred compacted portion.

FIGS. 4, 5 and 6 illustrate a particularly preferred embodiment of the present invention. Basically, the diaper 10 shown in FIGS. 4, 5 and 6 is constructed as hereinbefore described with like numbers referring to like parts. In the preferred embodiment illustrated in FIGS. 4, 5 and 6, however, the diaper 10 is provided with an elastic member 59 positioned at the leakage resistant members 22 which are affixed at the first and second longitudinal sides 37 and 38.

In the preferred embodiment illustrated in FIGS. 4, 5 and 6, the elastic member 59 is operatively associated with the leakage resistant member 22 in an elastically contractible condition so that in a normally unrestrained configuration, elastic member 59 effectively contracts or gathers the facing sheet 21 and the backing sheet 23 to provide an elasticized contractible line through the leakage resistant member 22. The elastic member 59 can be operatively associated with the leakage resistant member 22 in at least two ways, i.e., by stretching the elastic member 59 to its stretched condition and affixing it to the leakage resistant member 22 while the leakage resistant member 22 is in an uncontracted or stretched condition, or by contracting the leakage resistant member 22—for example, by pleating it—and fixing the elastic member 59 to the contracted leakage resistant member 22 or the elastic member 59 is in its relaxed or unstretched condition.

By positioning the elastic member 59 at the leakage resistant members 22 at the first and second longitudinal sides 37 and 38, the diaper 10 is provided with elasticized portions which when the diaper is worn by an infant, form elasticized leg cuffs. An elastic member 59 to provide the proper elasticity in the leakage resistant member 22 should have a tensional force within in its prestretched condition in the range of from about 10 to about 315 grams/cm of width and preferably in the range of from about 80 to about 160 grams/cm of width.

The elastic member 59 is preferably manufactured from thermoplastic elastomers such as styrene-butadine block copolymers or ethylene-propylene elastomers although many other materials such as natural rubbers, synthetic elastomers (e.g., spandex fibers), elastomeric foams or heat shrink flexible films may also be used. The elastic member 59 is preferably a single sheet of material of from about 0.001 inches to about 0.010 inches (about 0.025 mm to about 0.25 mm) thick.

The elastic member 59, as shown in FIGS. 4, 5 and 6, is operatively associated with the leakage resistant member 22 by interposing the elastic member 59 between the facing sheet 21 and the backing sheet 23 and by securing the elastic member 59 to the facing sheet 21 and preferably to the backing sheet 23. Any suitable means may be used to affix the elastic member 59 to the leakage resistant member 22. For example, the elastic member 59 may be affixed to the leakage resistant member 22 by using ultrasonic bonding techniques as are well known in the art. Preferably, the elastic member 59 is affixed to the compacted portion 54 of the facing sheet 21 only. Therefore, the uncompacted portion 55 of the facing sheet 21 is not adhered to the elastic member 59.

As hereinbefore stated, it is advantageous to have the compacted portion 54 disposed below the wearer contacting surface 58. When the elastic member 59 is provided, however, the compacted portion 54 may buckle and project toward the diaper wearer to such an extent that the compacted portion 54 actually touches the diaper wearer's skin. Accordingly, a preferred pattern for the compacted portion 54 will maintain the compacted portion 54 in a position below the wearer contacting surface 58 and will enhance the elevational differences between the compacted portion 54 and the wearer contacting surface 58 by causing a multiplicity of pillows 60 to be formed when the elastic member 59 is contracted. The pillows 60 are the uncompacted portions 55 of the facing sheet 21 which have been made to buckle and project toward the diaper wearer. When placed against the wearer, the skin of the wearer will contact the upper most portions of the pillows 60. These portions therefore form the wearer-contacting surface 58.

Figure 7:
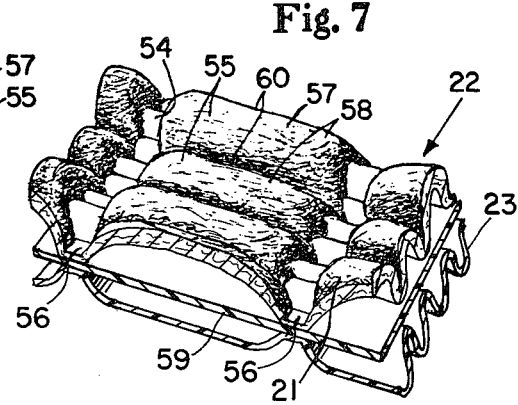
FIG. 7 is a perspective view of the leakage resistant member of FIG. 6 in a gathered configuration.

FIG. 6 is a plan view of a segment of the leakage resistant member 22 in an ungathered configuration. FIG. 6 shows a preferred compacted portion 54 comprising a multiplicity of continuous bands 56 defining reservoirs 57 therebetween. As hereinbefore described, the compacted portion 54 is affixed to the elastic member 59 (not shown in FIG. 6) and preferably is also affixed to the backing sheet 23 (not shown in FIG. 6) while the uncompacted portion 55 is not so fixed. As the elastic member 59 contracts, the facing sheet 21 is gathered. As the facing sheet 21 gathers, it will buckle. Because the uncompacted portion 55 is not affixed to the elastic member 59, it can freely buckle thereby forming pillows 60 as can be seen in FIG. 7. FIG. 7 is a perspective view of the leakage resistant member 22 shown in FIG. 6 in a gathered configuration (i.e., the elastic member 59 has been allowed to relax). Those areas of the pillows 60 which contact the wearer when the diaper is worn, form the wearer-contacting surface 58.

As can be seen in FIG. 7, the compacted portion 54 is disposed below the wearer-contacting surface 58 and is therefore prevented from contacting the skin of the diaper wearer. As used herein the term "disposed below" means that the compacted portion 54 is farther from the skin of the wearer than is the wearer-contacting surface 58 which contacts the wearer's skin when the diaper 10 is worn. It is believed that two factors make a major contribution to the preferred gathering of the facing sheet 21 whereby the compacted portion 54 is kept below the wearer-contacting surface 58. First, since the compacted portion 54 is affixed to the elastic member and preferably also affixed to the backing sheet 23, in order to buckle along the compacted portion 54, both the elastic member 59 and the backing sheet 23 must also buckle. On the other hand, the uncompacted portion 55 is free to buckle without deforming any other component of the leakage resistant member 22. Accordingly, the compacted portion 54 will not readily buckle out of the plane of the elastic member 59 while the uncompacted portion 55 will readily buckle away from the elastic member 59. The uncompacted portion 55 will buckle with a low frequency but high amplitude thereby forming pillows 60 while, by comparison, the compacted portion 54 will tend to buckle with a high frequency but low amplitude. Amplitude refers to the distance away from the elastic member 59.

The second factor contributing to the preferred gathering of the facing sheet 21 is the combined effect of the relative stiffnesses and compressive load distributions of the compacted portion 54 and the uncompacted portion 55. More specifically, since the compacted portion 54 has been modified so as to alter the flow pattern of liquid, the compacted portion 54 will generally differ in bending stiffness from the uncompacted portion 55. Also the compacted portion 54 is affixed to the elastic member 59 and therefore assumes the greater share of the compressive forces induced by the contraction of the elastic member 59. Because of the inherent stiffness and the compressive load concentration differences between the compacted portion 54 and the uncompacted portion 55, the compacted portion 54 will tend to buckle with a higher frequency but lower amplitude than the uncompacted portion 55. Buckling is a well known failure mode for columns and other members subjected to a compressive force and is described in H. Rothbart, *Mechanical Design and Systems Handbook*, Section 15 (1964), and T. Baumeister and L. Marks, *Standard Handbook for Mechanical Engineers*, Sections 5-21 (7th Ed. 1967), which publications are incorporated herein by reference.

Figure 8:
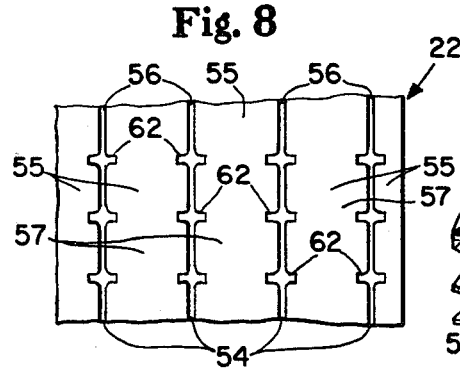
FIG. 8 is a plan view of a segment of the leakage resistant member in an ungathered configuration showing an alternatively preferred compacted portion.

In view of the foregoing, many alternative patterns for the compacted portion 54 will suggest themselves to one skilled in the art. For example, FIG. 8 is a plan view of a segment of the leakage resistant member 22 in an ungathered configuration showing an alternatively preferred compacted portion 54. As can be seen in FIG. 8, the facing sheet 21 of the leakage resistant member 22 has a compacted portion 54 and an uncompacted portion 55. The compacted portion 54 comprises a multiplicity of continuous bands 56 having expanded areas 62 which are simply widened sections of the band 56. The bands define reservoirs 57 therebetween.

Figure 9:
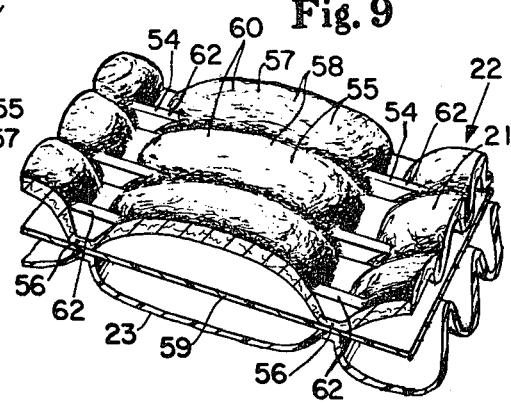
FIG. 9 is a perspective view of the leakage resistant member of FIG. 8 in a gathered configuration.

As can be seen in FIG. 9, which is a perspective view of the leakage resistant member 22 shown in FIG. 8 in a gathered configuration, the compacted portion 54 is affixed to the elastic member 59 and preferably is also affixed to the backing sheet 23 while the uncompacted portion 55 is not affixed to either the elastic member 59 or the backing sheet 23. As the elastic member 59 contracts, the facing sheet 21 is gathered. As hereinbefore described, the uncompacted portion 55 buckles with a low frequency but high amplitude compared to the compacted portion 54 thereby forming pillows 60. Those areas of the pillows 60 which contact the wearer when the diaper is worn, form the wearer-contacting surface 58.

The compacted portion 54 having buckled at a lower amplitude than the uncompacted portion 55, will be disposed below the wearer-contacting surface 58. The expanded areas 62 provide additional control of the buckling frequency, amplitude and regularity of the compacted portion 54. Accordingly, the expanded areas 62 may be positioned so as to provide a more regular buckling pattern than is achievable with a band not having expanded areas.

Expanded areas 62 which are generally rectangular having a length dimension of 0.100 inches (2.5 mm) and a width dimension of 0.030 inches (0.76 mm) placed on a band 56 having a width of 0.030 inches (0.76 mm) have been used and found to be satisfactory. The expanded areas were placed 0.25 inches (6.3 mm) center to center with the long dimension of the expanded areas 62 perpendicular to the length of the band 56. The bands 56 were spaced 0.375 inches (9.5 mm) apart.

Figure 10:
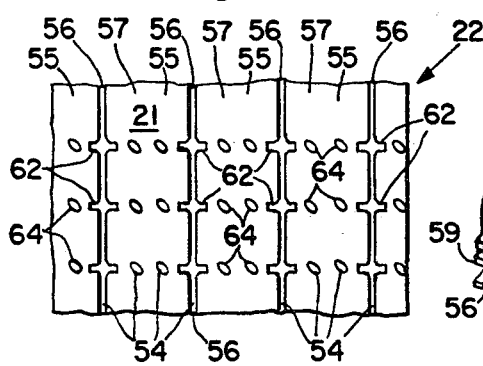
FIG. 10 is a plan view of a segment of the leakage resistant member in an ungathered configuration showing an alternatively preferred compacted portion.

FIG. 10 is a plan view of a segment of the leakage resistant member 22 in an ungathered configuration showing another alternatively preferred compacted portion 54. As can be seen in FIG. 10, facing sheet 21 of the leakage resistant member 22 has a compacted portion 54 and an uncompacted portion 55. The compacted portion 54 comprises a multiplicity of continuous bands 56 having expanded areas 62 and a multiplicity of disconnected areas 64. The bands 56 define reservoirs 57 therebetween which are interrupted by the disconnected areas.

Figure 11:
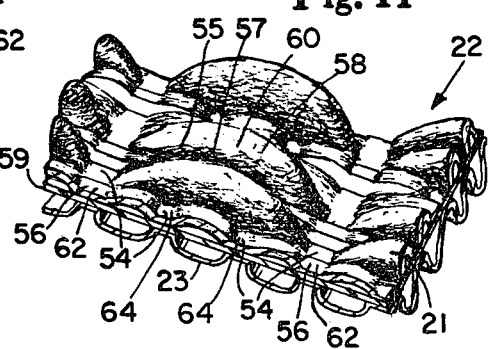
FIG. 11 is a perspective view of the leakage resistant member of FIG. 9 in a gathered configuration.

As can be seen in FIG. 11, which is a perspective view of the leakage resistant member 22 shown in FIG. 10 in a gathered configuration, the compacted portion 54 is affixed to the elastic member 59 and preferably affixed to the backing sheet 23 while the uncompacted portion 54 is not affixed to either the elastic member 59 or the backing sheet 23. As the elastic member 59 contracts, the facing sheet 21 is gathered. As hereinbefore described, the uncompacted portion 55 buckles with a low frequency but high amplitude compared to the compaction portion 54 thereby forming pillows 60. Those areas of the pillows 60 which contact the wearer when the diaper is worn form the wearer-contacting surface 58.

The compacted portions 54 having buckled at a lower amplitude than the uncompacted portion 55 will be disposed below the wearer-contacting surface 58. The expanded areas 62 provide additional control of the buckling frequency, amplitude, and regularity of the compacted portion 54. Accordingly, the expanded areas 62 may be positioned so as to provide a more regular buckling pattern than is achievable with a band not having expanded areas. The disconnected areas 64 provide additional control over the formation of pillows 60 as the uncompacted area 55 is gathered. Accordingly, the disconnected areas 64 are positioned so as to encourage the formation of pillows 60 which will retain their shape and loft as the leakage resistant member 22 is placed against the skin of the diaper wearer.

While not wishing to be bound by any one theory describing the operation of the present invention, it is believed that the improvement and liquid containment is achieved in the manner now to be described.

In use, the diaper 10 is placed between the legs of the diaper wearer and a back waist portion 32 and the front waist portion 33 are drawn and fastened about the diaper wearer's waist using any suitable means such as adhesive tapes 39. When the diaper 10 of the present invention is applied to an infant, it exhibits improved liquid containment. As urine is discharged onto the topsheet portion 12, some of the urine penetrates the topsheet 12 where it is absorbed by the absorbent core 14 (absorbed urine), some of the urine flows on the surface of the topsheet portion 12 (surface urine), some of the urine is absorbed by and wicks laterally through the topsheet portion 12 and some of the urine flows into capillary channel formed at the interface between the topsheet 12 and the skin of the diaper wearer.

The absorbed urine migrates throughout the absorbent core 14 moving from the point the discharge (i.e., the crotch area 34) toward the first and second longitudinal side edges 37 and 38. Eventually, the absorbed urine reaches the edge of the absorbent core 14. Since the leakage resistant member 22 is positioned outward from the absorbent core 14 the absorbed urine is retarded from reaching the periphery 17 of the diaper 10.

The surface urine, likewise, moves from the point of discharge toward the first and second longitudinal side edges 37 and 38 on the surface of the topsheet portion 12. As the surface urine approaches the first and second longitudinal side edges 37 and 38, respectively, the compacted portions 54 will be contacted. Having a greater capillary attraction for liquid than does the uncompacted portion 55, the compacted portion 54 will cause the surface urine to be absorbed by and to wick laterally along the continuous band 56 rather than continue to flow toward the first and second longitudinal side edges 37 and 38 of the diaper 10. As the local areas of the bands 56 become saturated, the surface urine may overcome the retarding effect of the band 56 and may flow into and be contained by the reservoir 57. As the reservoir 57, in turn, becomes saturated, the surface urine will encounter a second band 56 and again will be absorbed by and wick laterally along the band 56. In this manner, liquid is retarded or prevented from reaching the first and second longitudinal side edges 37 and 38 of the diaper 10.

Liquid is retarded from flowing along the capillary channel formed between the topsheet portion 12 and the skin of the diaper wearer by the elevational difference between the compacted portion 54 and the uncompacted portion 55 of the liquid of the leakage resistant member 22. Thus, liquid flowing between the wearer's skin and the topsheet 12 will encounter a band 56 which in the preferred embodiment illustrated in FIGS. 1 and 2 is depressed below the wearer-contacting surface and is therefore not in contact with the wearer's skin. Thus, a discontinuity is created between the wearer's skin and the topsheet portion 12. This discontinuity interrupts the capillary channel and retards further liquid flow toward the first and second longitudinal sides edges 37 and 38. In the embodiment illustrated in FIGS. 4 and 5, the compacted portion 54 is maintained below the wearer-contacting surface 58 so that a discontinuity is again created even though the elastic member 59 tends to press the compacted portion 54 into contact with the diaper wearer's skin.

Finally, urine which is absorbed interstitially by the topsheet portion 12 wicks laterally through the topsheet portion 12 toward the first and second longitudinal side edges 37 and 38. As in the instance of the surface urine, the urine absorbed by the topsheet portion 12 encounters a compacted portion 54 which causes the urine to wick laterally along the band 56. The urine absorbed by the topsheet portion 12 is thereby prevented from reaching the first and second longitudinal side edges 37 and 38.

It will be understood by those skilled in the art that the present invention has been described with reference to exemplary embodiments and that variations or modifications can be effected in the described embodiments without departing from the spirit and scope of the invention.

For example, several components of the diaper 10 hereinbefore described as individual components may be combined into a single component. FIG. 12 is a section view of an alternatively preferred embodiment of the present invention taken along a section line corresponding to section 5—5 of FIG. 4. FIG. 12 shows the topsheet portion 12 and the backsheet portion 16 of the outer covering layer 11 extending beyond the edge of the absorbent core 14 and being joined by a peripheral seam 20 at the peripheral edge 17. The leakage resistant member 22 has a facing sheet 21 which is integral with and a part of the topsheet portion 12. The elastic member 59 is affixed to the compacted portion 54 as hereinbefore described.

FIG. 13 is a section view of an alternatively preferred embodiment of the present invention taken along a section corresponding to section 5—5 of FIG. 4. FIG. 13 shows the topsheet portion 12 extending to the edge of the absorbent core 14 while the backsheet portion 16 wraps around the edge of the absorbent core 14 and is joined to the topsheet portion 12 by a peripheral seam 20. The leakage resistant member 22 has a facing sheet 21 having a compacted portion 54. The compacted portion 54 is affixed to the backing sheet 23. In the preferred embodiment shown in FIG. 13 the facing sheet 23 is manufactured from an elastic material and, therefore, the facing sheet 23 is also the elastic member 59. The leakage resistant member 22 is affixed to the outer covering layer 11 along the first end portion 24.

What is claimed is:

1. A disposable diaper comprising:
    an outer covering layer;
    an absorbent core means for absorbing liquids, said absorbent core means being encased in said outer covering layer;
    a peripheral edge comprising a first longitudinal side edge and a second longitudinal side edge; and
    a multiplicity of leakage resistant members, one of said leakage resistant members being affixed at said first longitudinal side edge and one of said leakage resistant members being affixed at said second longitudinal side edge, said leakage resistant member comprising a fibrous facing sheet, a liquid impermeable backing sheet underlaying said facing sheet, and an elastic member interposed between said facing sheet and said backing sheet, said facing sheet having a compacted portion and an uncompacted portion, said compacted portion comprising a multiplicity of continuous bands which redirect liquid away from said peripheral edge from which leakage may occur, said elastic member being affixed to said compacted portion and being affixed to said backing sheet, said elastic member gathering said facing sheet when said elastic member is unrestrained, said uncompacted portion forming pillows when said facing sheet is gathered, said facing sheet having a wearer-contacting surface and said compacted portion being disposed below said wearer-contacting surface.

2. The disposable diaper of claim 1 wherein the ratio of the caliper of said uncompacted portion to the caliper of said compacted portion is 1.5:1.

3. The disposable diaper of claim 1 wherein said continuous bands have expanded areas.

4. The disposable diaper of claim 3 wherein said bands have disconnected areas.

5. A disposable diaper comprising:
    an outer covering layer;
    an absorbent core means for absorbing liquids, said absorbent core means being encased in said outer covering layer;
    a peripheral edge comprising a first longitudinal side edge and a second longitudinal side edge; and
    a multiplicity of leakage resistant members, one of said leakage resistant members being affixed at said first longitudinal side edge and one of said leakage resistant members being affixed at said second longitudinal side edge, said leakage resistant member comprising a fibrous facing sheet, a liquid impermeable backing sheet underlaying said facing sheet, and an elastic member interposed between said facing sheet and said backing sheet, said facing sheet having a compacted portion and an uncompacted portion, said compacted portion comprising an array of discrete areas which render the path followed by liquid tortuous, said elastic member gathering said facing sheet when said elastic member is unrestrained, said uncompacted portion forming pillows when said facing sheet is gathered, said facing sheet having a wearer-contacting surface and said compacted portion being disposed below said wearer-contacting surface.

* * * * *

UNITED STATES PATENT AND TRADEMARK OFFICE
CERTIFICATE OF CORRECTION

PATENT NO. : 4,397,645
DATED : August 9, 1983
INVENTOR(S) : Kenneth Barclay Buell It is certified that error appears in the above-identified patent and that said Letters Patent are hereby corrected as shown below:

Column 1, line 11, "contain" should read -- contact --.

Column 4, line 24, "portions" should read -- portion --.

Column 7, line 19, "lonitudinal" should read -- longitudinal --.

Column 7, line 32, "lonitudinal" should read -- longitudinal --.

Column 13, line 42, "compaction" should read -- compacted --.

Signed and Sealed this

Twenty-seventh Day of November 1984

[SEAL]

Attest:

GERALD J. MOSSINGHOFF

Attesting Officer

Commissioner of Patents and Trademarks